United States Patent
Soares Da Silva et al.

(10) Patent No.: US 8,158,666 B2
(45) Date of Patent: Apr. 17, 2012

(54) PROCESS FOR THE PREPARATION OF (R)-5-(2-AMINOETHYL)-1-(6,8-DIFLUOROCHROMAN-3-YL)-1,3-DIHYDROIMIDAZOLE-2-THIONE

(75) Inventors: Patrício Manuel Vieira Araújo Soares Da Silva, Porto (PT); Alexander Beliaev, Mindelo (PT); David Alexander Learmonth, Alfena (PT)

(73) Assignee: Bial-Portela & C.A., S.A., S. Mamede do Coronado (PT)

( * ) Notice: Subject to any disclaimer, the term of this patent is extended or adjusted under 35 U.S.C. 154(b) by 89 days.

(21) Appl. No.: 12/525,043

(22) PCT Filed: Jan. 31, 2008

(86) PCT No.: PCT/PT2008/000006
§ 371 (c)(1), (2), (4) Date: Oct. 13, 2009

(87) PCT Pub. No.: WO2008/094056
PCT Pub. Date: Aug. 7, 2008

(65) Prior Publication Data
US 2010/0121073 A1 May 13, 2010

(30) Foreign Application Priority Data
Feb. 1, 2007 (GB) .................................. 0701966.4

(51) Int. Cl.
*A61K 31/4178* (2006.01)
*C07D 233/12* (2006.01)
(52) U.S. Cl. ..................................... 514/386; 548/311.4
(58) Field of Classification Search .................. 514/386; 548/311.4
See application file for complete search history.

(56) References Cited

U.S. PATENT DOCUMENTS
5,438,150 A   8/1995   Bansal et al.

FOREIGN PATENT DOCUMENTS
WO   2004033447 A1     4/2004
WO   WO-2004/033447 A  *  4/2004
WO   2008094056 A1     8/2008

OTHER PUBLICATIONS

Beliaev, Alexandre, et al., "Synthesis and biological evaluation of novel, peripherally selective chromanyl imidazolethione-based inhibitors of dopamine 6-hydroxylase," J. Med. Chem., 2006, vol. 49, pp. 1191-1197.*
Beliaev, Alexandre, et al., "Synthesis and biological evaluation of novel, peripherally selective chromanyl imidazolethione-based inhibitors of dopamine β-hydroxylase," J. Med. Chem., 2006, vol. 49, pp. 1191-1197, American Chemical Society.
Gall, Martin, et al., "Synthesis of aminoalkyl-substituted imidazo[1,2-a]-and imidazo[1,5-a]benzodiazepines," J. Org. Chem., 1981, vol. 46, pp. 1575-1585, American Chemical Society.
Foreign communication from the priority application—International Search Report, PCT/PT2008/000006, May 14, 2008, 3 pages.
Foreign communication from the priority application—Written Opinion, PCT/PT2008/000006, Aug. 1, 2009, 6 pages.
Foreign communication from the priority application—International Preliminary Report on Patentability, PCT/PT2008/000006, Aug. 4, 2009, 6 pages.

* cited by examiner

*Primary Examiner* — Kamal Saeed
*Assistant Examiner* — Janet L Coppins
(74) *Attorney, Agent, or Firm* — Conley Rose, P.C.; Rodney B. Carroll

(57) ABSTRACT

A process for making (R)-5-(2-aminoethyl)-1-(6,8-difluorochroman-3-yl)-1,3-dihydroimidazole-2-thione and pharmaceutically acceptable salts thereof, and for making intermediates useful in the formation of said compound.

16 Claims, 4 Drawing Sheets

PROCESS FOR THE PREPARATION OF (R)-5-(2-AMINOETHYL)-1-(6,8-DIFLUOROCHROMAN-3-YL)-1,3-DIHYDROIMIDAZOLE-2-THIONE

CROSS-REFERENCE TO RELATED APPLICATIONS

This application is a filing under 35 U.S.C. 371 of International Application No. PCT/PT2008/000006 filed Jan. 31, 2008, entitled "Process for the Preparation of (R)-5-(2-Aminoethyl)-1-(6,8-Difluorochroman-3-YL)-1,3-Dihydroimidazole-2-Thione," claiming priority of Great Britain Application No. 0701966.4 filed on Feb. 1, 2007, which applications are incorporated by reference herein in their entirety.

FIELD OF THE INVENTION

This invention relates to a process for making (R)-5-(2-aminoethyl)-1-(6,8-difluorochroman-3-yl)-1,3-dihydroimidazole-2-thione, and pharmaceutically acceptable salts thereof, especially the hydrochloride salt. The invention also relates to a process for making intermediates useful in the formation of said compound, and to the intermediates, per se.

BACKGROUND OF THE INVENTION (R)-5-(2-aminoethyl)-1-(6,8-difluorochroman-3-yl)-1,3-dihydroimidazole-2-thione hydrochloride is described in WO2004/033447, and is useful as a medicament for treating disorders where a reduction in the hydroxylation of dopamine to noradrenaline is of therapeutic benefit. Such disorders include cardiovascular disorders, for example, hypertension and chronic heart failure.

SUMMARY OF THE INVENTION

The present invention provides a process for manufacturing Form A and Form C (R)-5-(2-aminoethyl)-1-(6,8-difluorochroman-3-yl)-1,3-dihydroimidazole-2-thione hydrochloride.

Figure 1:
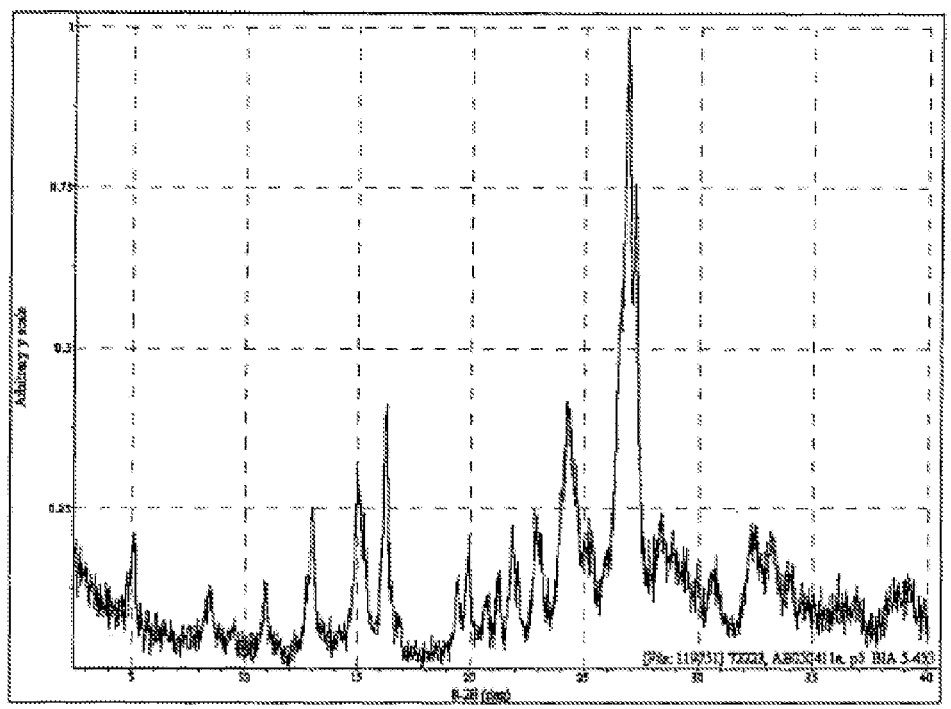

The crystalline form A of (R)-5-(2-Aminoethyl)-1-(6,8-difluorochroman-3-yl)-1,3-dihydroimidazole-2-thione hydrochloride has an XRPD pattern with peaks at 4.9, 8.3, 12.9, 15.0, 16.2, 19.8, 21.8, 22.9, 24.2 and 26.8±0.2 °2θ. The XRPD pattern is shown in FIG. 1.

Figure 2:
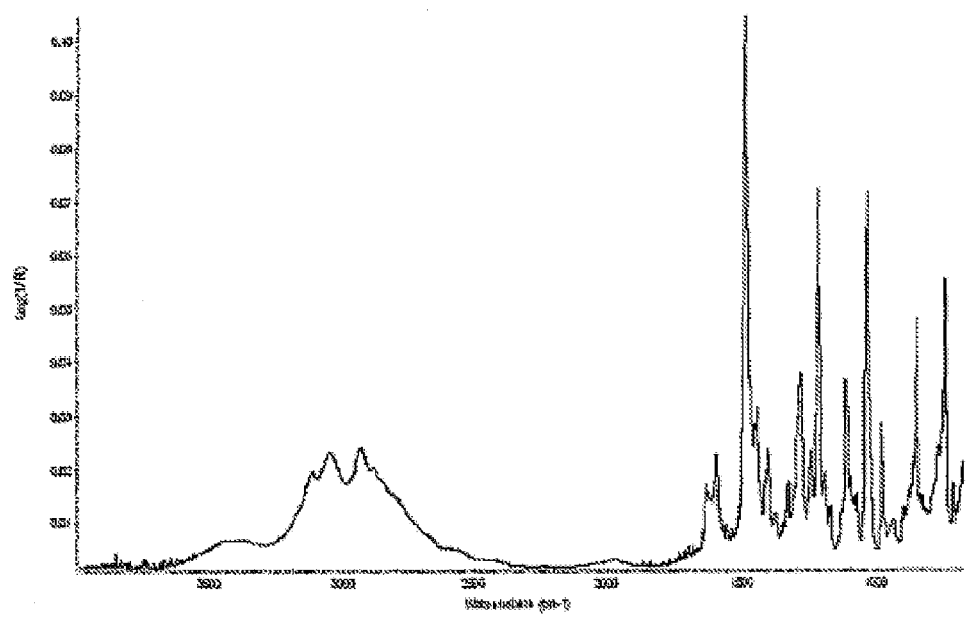

Furthermore, crystalline form A of (R)-5-(2-Aminoethyl)-1-(6,8-difluorochroman-3-yl)-1,3-dihydroimidazole-2-thione hydrochloride has characteristic FT-IR peaks at 3053.30, 2939.70, 1599.80, 1491.90, 1448.30 1406.10, 1330.70, 1287.60, 1244.50, 1220.70, 1194.00, 1117.50, 1039.50, 985.50, 851.80, 747.00 and 713.70 cm-1. The FT-IR spectrum is shown in FIG. 2.

Figure 3:
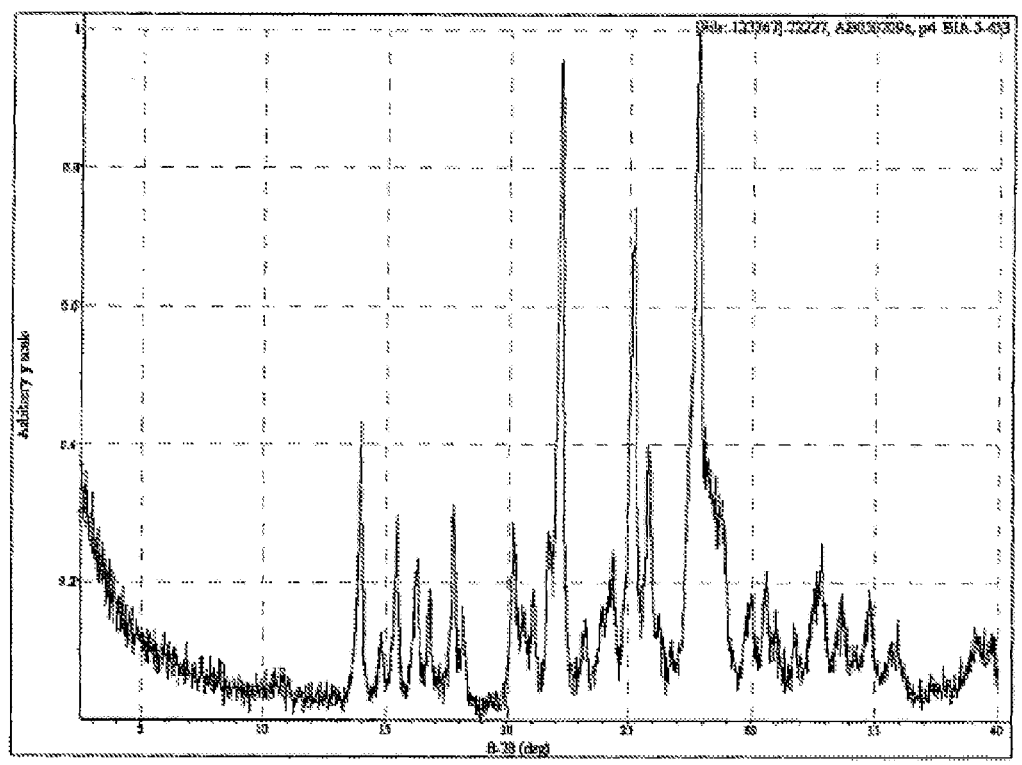
Figure 4:
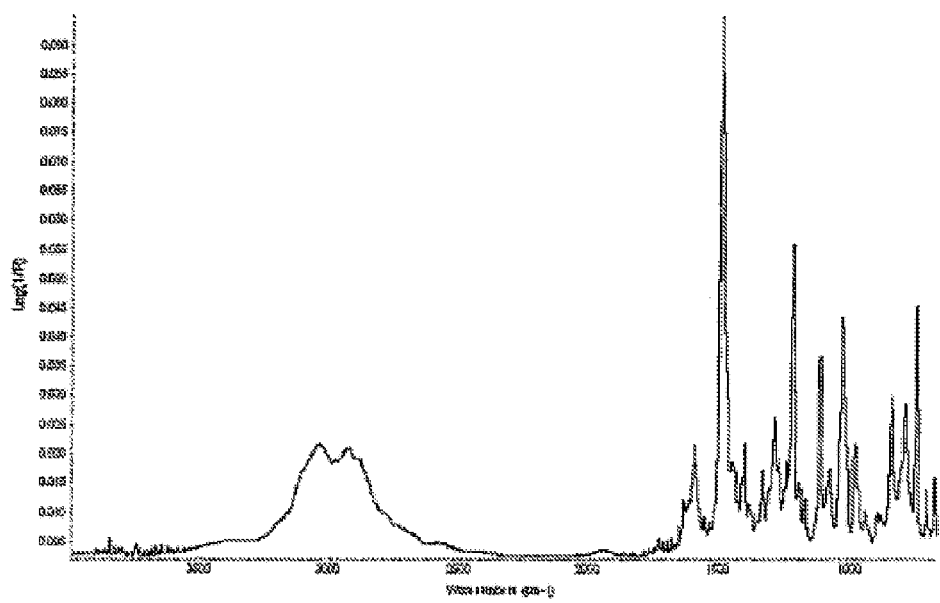

The crystalline form C of (R)-5-(2-Aminoethyl)-1-(6,8-difluorochroman-3-yl)-1,3-dihydroimidazole-2-thione hydrochloride has an XRPD pattern with peaks at 13.9, 15.3, 16.2, 16.7, 17.7, 18.1, 20.2, 21.0, 22.1, 24.2, 25.1 and 25.7±0.2 °2θ. The XRPD pattern is shown in FIG. 3. Furthermore, the crystalline form C of (R)-5-(2-Aminoethyl)-1-(6,8-difluorochroman-3-yl)-1,3-dihydroimidazole-2-thione hydrochloride has characteristic FT-IR peaks at 3041.70, 1596.50, 1492, 1403.40, 1333.80, 1290.90, 1220.2, 1173.20, 1117.4, 1078.10, 1033.4, 984.90 845.2, 792.6, 750.1 and 713.20 cm-1. The FT-IR spectrum is shown in FIG. 4.

DETAILED DESCRIPTION

According to one aspect of the invention there is provided a process for making a compound of formula 14:

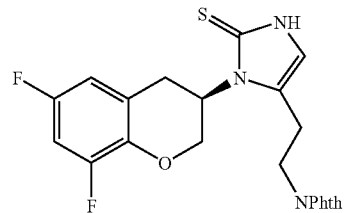

comprising reacting a compound of formula 8:

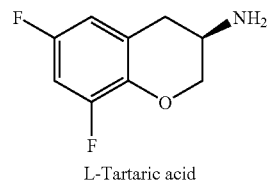

with a compound of formula 13:

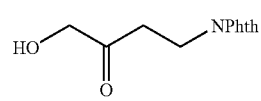

and a water soluble thiocyanate and an organic acid.

Compound 8 may be synthesised starting from L-serine methyl ester hydrochloride by condensation of its N-trityl derivative with 2,4-difluorophenol under Mitsunobu conditions followed by deprotection, ethoxycarbonylation of the resulting amino acid, Friedel-Crafts cyclization of N-protected derivative and reduction of the ethoxycarbonylamino ketone. The alkaline hydrolysis of ethyl carbamate gives 8:

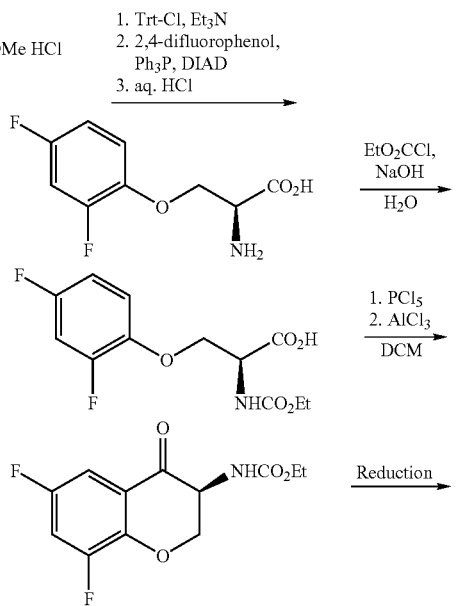

-continued

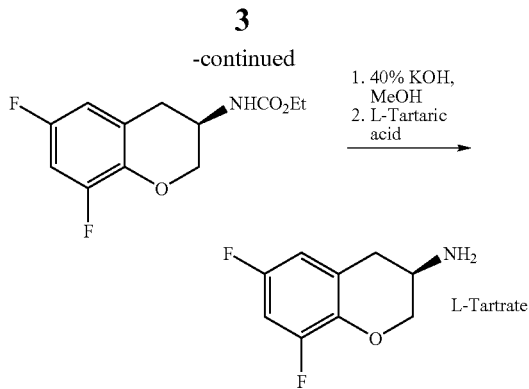

A method for producing the compound of formula 13 is described in Gall & Kamdar (1981) J. Org. Chem. 46, 1575-1585.

Preferably, the reaction is carried out at a temperature from 105° C. to 110° C.

The water soluble thiocyanate may be an alkali metal thiocyanate, preferably potassium thiocyanate.

The organic acid may also act as a solvent for the reaction. An additional inert solvent may be used, if desired. Preferably the organic acid is acetic acid.

It is preferred that the process includes the step of purifying the compound of formula 14.

According to another aspect of the invention there is provided a process for making a compound of formula 1:

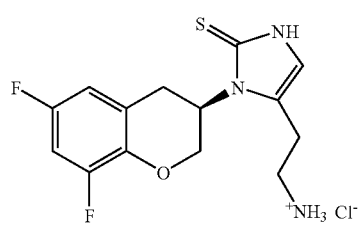

comprising reacting a compound of formula 14:

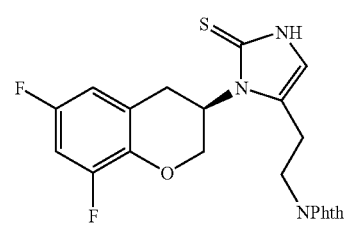

with an alkali metal borohydride in the presence of a solvent, followed by reaction with hydrochloric acid.

The alkali metal borohydride is preferably sodium borohydride. As an alternative, a quaternary ammonium borohydride may be used.

The solvent may be provided as any suitable inert solvent, and is preferably an alcohol, especially a $C_1$ to $C_6$ alcohol, or a chlorinated solvent, or a mixture thereof, optionally in combination with water. Most preferably, the solvent is a mixture of water, 2-propanol and dichloromethane.

In one preferred embodiment, the reaction with hydrochloric acid under conditions suitable to produce a crystalline form A of the compound of formula 1.

In another preferred embodiment, the reaction with hydrochloric acid under conditions suitable to produce a crystalline form C of the compound of formula 1.

It is to be noted that to form pharmaceutically acceptable salts other than the hydrochloride salt, an acid other than hydrochloric acid may be selected. Selection of a suitable acid and conditions is within the knowledge of the skilled person, and does not require undue experimentation. Alternatively, the salt, eg the hydrochloride salt, may be converted to the free base and isolated, or, optionally, converted to a still further pharmaceutically acceptable salt.

According to another aspect of the invention there is provided a compound of formula 14:

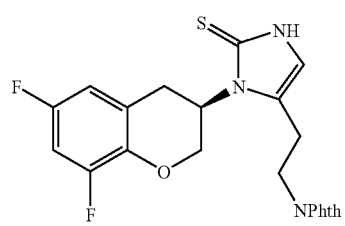

EXAMPLES

Reference is now made to the following examples.

Example 1

Preparation of (R)-2-{2-[3-(6,8-Difluorochroman-3-yl)-2-thioxo-2,3-dihydro-1H-imidazol-4-yl]ethyl-isoindole-1,3-dione (14)

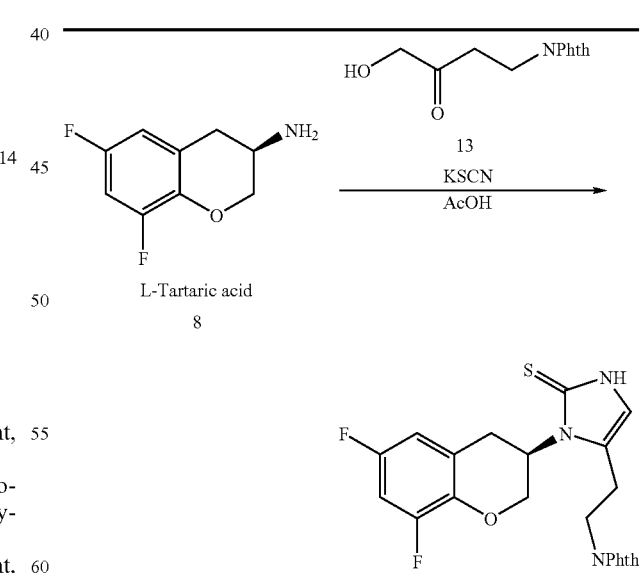

| Reagents and solvents: | Aminochroman tartrate 8 | 4.02 g (12.0 mmol) |
| --- | --- | --- |
| | Hydroxy ketone 13 | 3.36 g (14.4 mmol) |
| | Potassium thiocyanate | 1.40 g (14.4 mmol) |
| | Acetic acid | 48 mL |

A reactor was charged with solid reagents, acetic acid was added in one portion, the mixture was heated to 105-110° C. under nitrogen with stirring and kept under above conditions for 2 h. Water (24 mL) was added slowly with heating at ca. 90° C. (crystallisation occurred), the suspension was cooled in the ice-bath with stirring, stirred for 0.5 h in ice, water (24 mL) was added slowly and stirring continued for 1 h. The precipitate was collected, washed with AcOH-water (1:1 v/v), water, dried at 50-60° C. in vacuum. The resulting solid (5.25 g, 99%) was dissolved under reflux in the mixture of IPA (48 mL) and DCM (72 mL), the insoluble material (K tartrate) was filtered off, the filtrate was evaporated on a rotavap at ca. 50° C. and 500 mbar until crystallisation occurred, then heating was removed and evaporation was continued to remove the residual DCM. The suspension was left in the fridge overnight, the crystals were collected, washed with IPA, dried in vacuum at 50° C. Yield 3.40 g (64%).

Example 2

Preparation of (R)-5-(2-aminoethyl)-1-(6,8-difluoro-chroman-3-yl)-1,3-dihydroimidazole-2-thione hydrochloride (BIA 5-453) (1), modification for Form A preparation

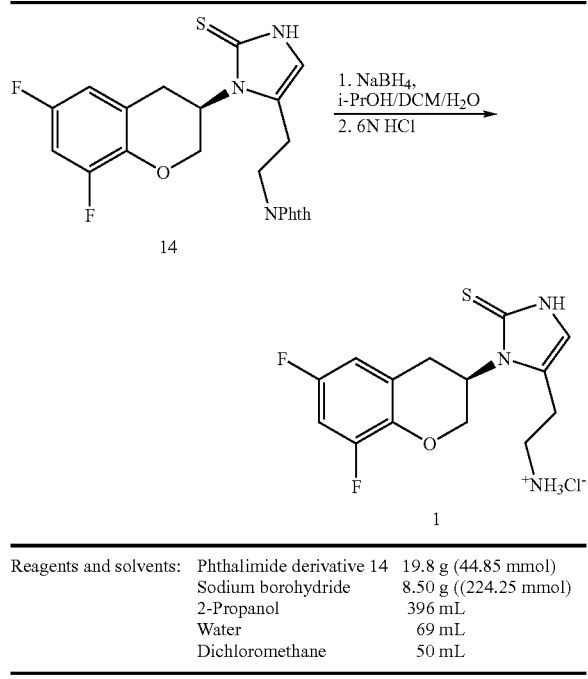

| Reagents and solvents: | Phthalimide derivative 14 | 19.8 g (44.85 mmol) |
| --- | --- | --- |
| | Sodium borohydride | 8.50 g ((224.25 mmol) |
| | 2-Propanol | 396 mL |
| | Water | 69 mL |
| | Dichloromethane | 50 mL |

To a suspension of 14 in the mixture of 2-propanol, water and DCM NaBH₄ was added at 18° C. in portions during 1 min with stirring (temp. raised to 27.5° C. in 1 h). The mixture was stirred at 18-20° C. for 16 h (almost clear solution in 1 h). The mixture was cooled in the ice bath, 6N HCl (39.6 mL, 237.6 mmol) was added dropwise keeping the temp. below 10° C. The mixture was stirred for 15 min, the solid was filtered off, the filter cake was washed with DCM (300 mL) (4.9 g of solid obtained). To the mother liquor 5N NaOH (60 mL) was added, the mixture was stirred for 15 min, organic upper layer was separated, washed with brine, filtered to remove minimum amount of solid. To the resulting clear solution 6N HCl (40 ml) was added, DCM was distilled off until the vapour temperature reached 76-78° C., the mixture was stirred under reflux for 1.5 h and cooled to r.t. Water (300 mL) was added, IPA was removed on a rotavap (420 mL collected), the residue was washed with EtOAc-petroleum ether (2:1 v/v) mixture (200 and 100 mL). After second washing crystallisation in aqueous phase started. 6N HCl (40 mL) was added, the suspension was cooled in ice for 1 h with stirring, the precipitate was collected, washed with cold 3N HCl (75 mL), cold IPA (50 mL), dried in vacuum at 50° C. Yield 11.58 g (73%).

Example 3

Preparation of (R)-5-(2-aminoethyl)-1-(6,8-difluoro-chroman-3-yl)-1,3-dihydroimidazole-2-thione hydrochloride (BIA 5-453) (1), modification for Form C preparation

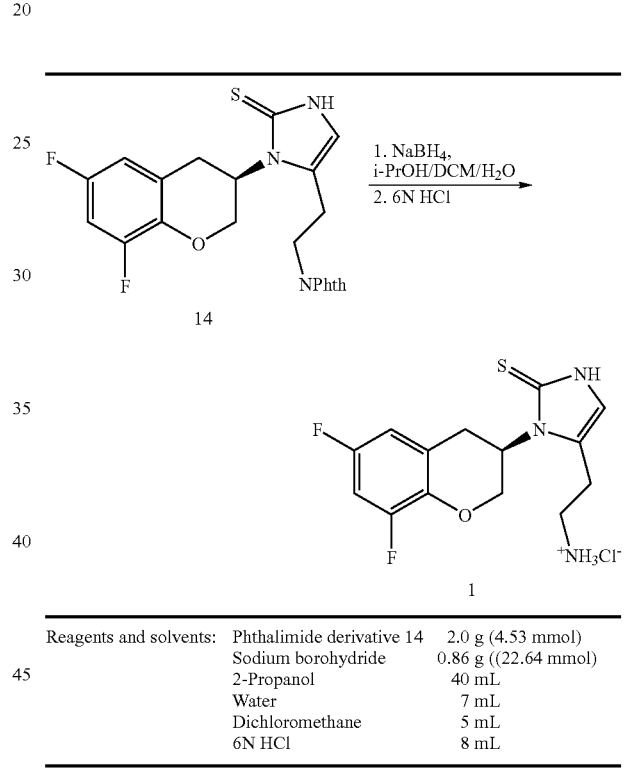

| Reagents and solvents: | Phthalimide derivative 14 | 2.0 g (4.53 mmol) |
| --- | --- | --- |
| | Sodium borohydride | 0.86 g ((22.64 mmol) |
| | 2-Propanol | 40 mL |
| | Water | 7 mL |
| | Dichloromethane | 5 mL |
| | 6N HCl | 8 mL |

To a suspension of 14 in the mixture of 2-propanol, water and DCM NaBH₄ was added at 20° C. in portions during 1 min with stirring (temp. rised to 22° C.). The mixture was stirred at 20° C. for 16 h (clear solution in 0.5 h), 6N HCl was added dropwise. DCM was distilled off until head temperature reached 76-78° C., the mixture was stirred under reflux for 1.5 h and cooled to room temperature. Water (30 mL) was added, 2-propanol was removed on a rotavap, the residue was washed with EtOAc-petroleum ether (2:1 v/v) mixture (2×20 mL). To the aqueous layer 10% 2-propanol in DCM solution (40 mL) was added with stirring followed by 5N NaOH to pH 9-10. Organic layer was separated, dried (MgSO₄), evaporated to dryness. The residue was dissolved with heating in the mixture of abs. EtOH (15 mL) and 3M HCl in abs. EtOH (1.5 mL, pH of the mixture ca. 2). The resulting solution was stirred at 65-70° C. for 2 h, the crystals were collected, washed with EtOH, dried in vacuum at 40° C. Yield 1.12 g (71%).

Example 4

(R)-5-(2-Aminoethyl)-1-(6,8-difluorochroman-3-yl)-1,3-dihydroimidazole-2-thione (R)-5-(2-Aminoethyl)-1-(6,8-difluorochroman-3-yl)-1,3-dihydroimidazole-2-thione hydrochloride (9.64 g, 27.72 mmol) was dissolved in water (160 ml) at 40-45° C. with stirring. To the resulting solution 2-propanol (64 ml) was added, the mixture was cooled to 35-38° C., dichloromethane (256 ml) was added followed by 1N NaOH (28 ml, 28 mmol) and the stirring continued for 10-15 min. Lower organic phase was separated, dried over MgSO4 and evaporated under reduced pressure to approx. 40 ml. The resulting suspension was diluted with petroleum ether (200 ml), the precipitate was collected, was with petroleum ether on the filter, dried in vacuum. Yield 7.8 g (91%), mp 192-5° C. (dec).

The free base can be converted to a desired salt using techniques known to those skilled in the art.

What is claimed is:

1. A process for making a compound of formula 14:

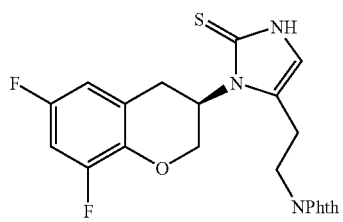

14 comprising reacting a compound of formula 8:

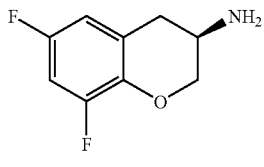

8

L-Tartaric acid with a compound of formula 13:

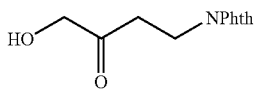

13 and a water soluble thiocyanate and an organic acid.

2. The process according to claim 1, wherein the reaction is carried out at a temperature from 105° C. to 110° C.

3. The process according to claim 1, wherein the water soluble thiocyanate is an alkali metal thiocyanate.

4. The process according to claim 3, wherein the alkali metal thiocyantate is potassium thiocyanate.

5. The process according to claim 1, wherein the organic acid is acetic acid.

6. The process according to claim 1, further comprising the step of purifying the compound of formula 14.

7. A process for making a compound of formula 1:

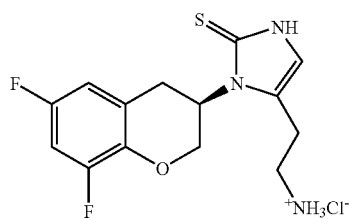

1 comprising reacting a compound of formula 14:

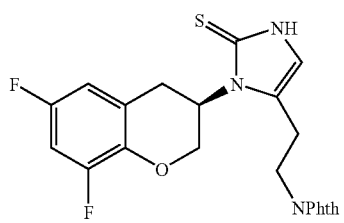

14 with an alkali metal borohydride in the presence of a solvent, followed by reaction with HCl.

8. The process according to claim 7, wherein the alkali metal borohydride is sodium borohydride.

9. The process according to claim 7, wherein the solvent is a mixture of water, 2-propanol and dichloromethane.

10. The process according to claim 7, comprising carrying out the reaction with hydrochloric acid under conditions suitable to produce a crystalline form A of the compound of formula 1.

11. The process according to claim 7, comprising carrying out the reaction with hydrochloric acid under conditions suitable to produce a crystalline form C of the compound of formula 1.

12. The process according to claim 7, wherein the compound of formula 14 is produced according to the process of comprising reacting a compound of formula 8:

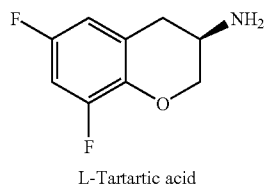

8

L-Tartaric acid with a compound of formula 13:

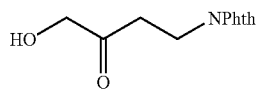

13 and a water soluble thiocyanate and an organic acid.

13. A process for making the free base of a compound of formula 1:

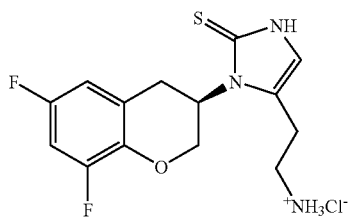

comprising reacting a compound of formula 14:

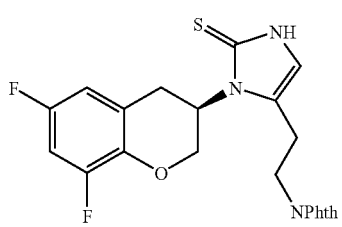

with an alkali metal borohydride in the presence of a solvent, followed by reaction with HCl, followed by reaction with a suitable base to produce the free base of the compound of formula 1.

14. The process according to claim 13, wherein the compound of formula 14 is produced according to the process comprising reacting a compound of formula 8:

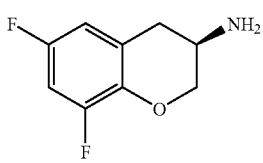

with a compound of formula 13:

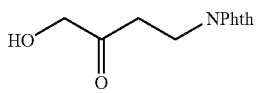

and a water soluble thiocyanate and an organic acid.

15. A compound of formula 14:

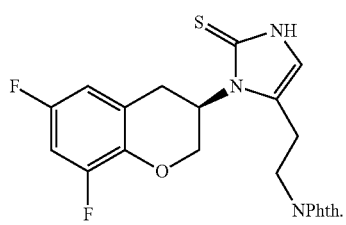

16. A compound of formula 8:

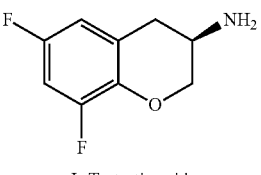

* * * * *